United States Patent [19]

Ray et al.

[11] Patent Number: 4,655,231

[45] Date of Patent: Apr. 7, 1987

[54] SNUFF AND PREPARATION THEREOF

[75] Inventors: Jon P. Ray; Michael P. Ellis, both of San Antonio, Tex.

[73] Assignee: Advanced Tobacco Products, Inc., San Antonio, Tex.

[21] Appl. No.: 569,281

[22] Filed: Jan. 9, 1984

[51] Int. Cl.$^4$ .............................................. A24B 15/16
[52] U.S. Cl. .................................... 131/359; 131/352; 131/369
[58] Field of Search ............... 131/359, 369, 352, 335, 131/270

[56] References Cited

U.S. PATENT DOCUMENTS

| | | |
|---|---|---|
| 1,599,787 | 9/1926 | Perkiss . |
| 2,139,839 | 12/1938 | McKinney . |
| 2,496,125 | 1/1950 | Griesman . |
| 2,809,634 | 10/1957 | Murai . |
| 3,422,819 | 1/1969 | Jones et al. .......................... 131/335 |
| 3,757,798 | 9/1973 | Lambert . |
| 3,870,794 | 3/1975 | Hutchinson et al. . |
| 3,877,468 | 4/1975 | Lichtneckert et al. . |
| 4,192,309 | 3/1980 | Poulsen . |
| 4,195,645 | 4/1980 | Bradley, Jr. et al. . |
| 4,203,454 | 5/1980 | Wutscher . |
| 4,284,089 | 8/1981 | Ray . |

OTHER PUBLICATIONS

Russell et al., "Nasal Nicotine Solution. A Potential Aid to Giving Up Smoking?", *British Medical Journal*, vol. 286, p. 683 (Feb. 26, 1983).

Wald, N. J. et al., "Serum Cotinine Levels in Pipe Smokers: Evidence Against Nicotine as a Cause of Coronary Heart Disease", *The Lancet*, p. 775, Oct. 10, 1981.

Russell, "Nicotine Intake and Its Regulation", *Journal of Psychosomatic Research*, vol. 24, p. 253, (Dec., 1979).

Russell et al., "A New Age for Snuff?" *The Lancet*, p. 474, Mar. 1, 1980.

Russell et al., "Nicotine Intake by Snuff Users", *British Medical Journal*, vol. 283, p. 814 (Sep. 26, 1981).

*Primary Examiner*—V. Millin
*Attorney, Agent, or Firm*—Arnold, White & Durkee

[57] ABSTRACT

An improved snuff containing substantially pure powdered salts of nicotine diluted with powdered organic sugars which is substantially absorbed by the nasal membranes when applied thereto. Flavoring and/or coloring agents are optionally present. The improved snuff is prepared by adding an acid to a nicotine solution, separating the nicotine salt from the solution, diluting the nicotine salt to a usable concentration, and optionally adding flavoring and/or coloring agents to enhance the fragrance and appearance of the improved snuff.

17 Claims, No Drawings

SNUFF AND PREPARATION THEREOF

BACKGROUND OF THE INVENTION

The present invention relates to an improved snuff useful in the nasal application of nicotine. The invention pertains to a rapid, pleasant and harmless mixture containing nicotine for nasal application which is absorbed by the nasal membranes. The invention further pertains to a method for preparing an improved snuff useful in the nasal application of nicotine.

Tobacco has been used for hundreds of years by many cultures throughout the world. Currently popular methods of use include smoking tobacco, such as in cigarettes, cigars or a pipe, chewing and sniffing. However, these methods have numerous disadvantages, including inherent health hazards and social unacceptability.

Medical research has established that nicotine is the active ingredient in tobacco. Small doses of nicotine provide the user with certain pleasurable effects resulting in the desire for additional doses. However, recent medical research published by Russell et al, Nasal Nicotine Solution: A Potential Aid to Giving Up Smoking?, *British Medical Journal*, vol. 286, p. 683 (Feb. 26, 1983), indicates that nicotine is not a carcinogen. There is also evidence that nicotine is not responsible for the high rate of death among cigarette smokers. For example, see Wald, N. J. et al, Serum Cotinine Levels in Pipe Smokers: Evidence Against Nicotine As Cause of Coronary Heart Disease, *The Lancet*, Oct. 10, 1981, p. 775. Thus, one who uses tobacco for the pleasurable effects of nicotine must also risk the dangers of coronary heart disease and cancer although there is speculation that such adverse side effects are in fact the result of naturally occurring tobacco components and of the by-products of combustion normally associated with the smoking habit.

Several techniques have been developed which allow the body to absorb small amounts of uncontaminated nicotine. These include nicotine chewing gum, nicotine tablets and nicotine vapor inhalants. There is evidence, however, that the degree of pleasure derived from nicotine is proportional to how rapidly the nicotine enters the blood stream of the user. Russell, Nicotine Intake and Its Regulation, *Journal of Psychosomatic Research*, Vol. 24, p. 253 (December, 1979). When nicotine is administered orally, it is absorbed by the lining of the mouth which is a relatively slow process. The inhalation of nicotine vapor allows nicotine to enter the body almost instantaneously through the lining of the lungs, but the manufacturing and packaging costs of such devices are relatively high compared to the subject invention.

On the other hand, the nasal administration of nicotine allows the absorption of the substance to occur approximately as rapidly as by inhalation. Russell et al., A New Age for Snuff?, *The Lancet*, Mar. 1, 1980, p. 474; Russell et al., Nicotine Intake by Snuff Users, *British Medical Journal*, Vol. 283, p. 814 (Sept. 26, 1981). Conventional nasal snuff, however, offers several disadvantages to the user. Because it is finely ground leaf material, its most significant drawback is that it is not water soluble and tends to form a brown, offensive coating on the inside of the user's nasal passages. Furthermore, because of the carcinogens found in tobacco, the use of snuff carries at least a slight risk of nasal cancer.

Recently, a liquid nasal nicotine solution has been developed by Russell et al, Nasal Nicotine Solution: A Potential Aid to Giving Up Smoking?, *British Medical Journal*, Vol. 286 at page 683 (Feb. 26, 1980). A two percent aqueous solution of nicotine was combined with a cellulose derivative to increase its viscosity and allow the mixture to remain in the user's nasal passages. Each dosage (0.1 milliter) was made up in a small plastic container which could be opened and squeezed for administration. The nasal solution has the disadvantages of being expensive to manufacture and inconvenient to use, requiring a conventional snuff user to change his established ritual.

Other methods of application of nicotine have developed a social acceptability. Examples of these are the oral use of so-called smokeless tobacco, some of which is contained in a porous pouch.

For the most part, the prior art has involved the development of various application devices as opposed to actual nicotine formulas. Examples of such devices which are known include: U S. Pat. No. 2,809,634 to Murai (pipe device used to atomize a material in solution which is inhaled); U.S. Pat. No. 4,192,309 to Poulsen (breath actuated inhalation device for dispensing a powdered medicament through the mouth or nasal cavity); U.S. Pat. No. 4,203,454 to Wutscher (an elaborate device for projecting snuff into the nostrils); U.S. Pat. No. 1,599,787 to Perkins (apparatus for nasal douche); and U.S. Pat. No. 2,496,125 to Griesman (nasal applicator device).

SUMMARY OF THE INVENTION

The present invention is a mixture containing one or more nicotine salts diluted to a usable concentration with harmless, water soluble constituents. The mixture is substantially absorbed by the nasal membranes. The form of the mixture is a white powder. The mixture may optionally be colored, flavored, or scented as desired.

The nicotine mixture of the invention is completely water soluble and leaves no residue in the nasal passages of the user when applied thereto. Because it is substantially and rapidly absorbed in the nasal passages, the improved snuff of the present invention is more pleasant to use and more socially acceptable than nicotine containing substances currently in use. The nicotine used in the mixture of the present invention is substantially pure, containing none of the carcinogenic or toxic substances which are inhaled or ingested with nicotine from unrefined tobacco sources.

The nicotine salts are prepared by reacting nicotine with an acid and removing the nicotine salt formed thereby. The nicotine salts are diluted to a usable concentration with a water soluble diluent. Optionally, coloring, flavoring, or scent may be added.

DETAILED DESCRIPTION OF THE INVENTION

Nicotine, a colorless liquid, may be obtained synthetically or it may be extracted from botanical sources such as, for example, tobacco. Regardless of the source, nicotine used in the invention should be refined so that it is substantially pure. The nicotine may be present in the improved snuff in any concentration. However, if the concentration is excessive it is difficult for the user to regulate the amount of nicotine inhaled or ingested. On the other hand, if the concentration of nicotine is too low, the user will have to apply an excessive amount of the nicotine mixture to his nasal passages. The preferred nicotine salt concentration in the improved snuff is 3% to 5% by weight.

Any acid which forms a water soluble salt with nicotine may be used as long as it is safe for human consumption and not unpleasant. The salt is preferably white or colorless. Organic acids, such as oxalic acid, benzoic acid, and salicylic acid, are preferred over inorganic acids because the mineral salts of nicotine are typically hygroscopic. Oxalic acid is the most preferred organic acid.

The improved snuff contains a diluent. The diluent must be water soluble so that it is readily absorbed by the nasal membranes. The diluent must also be safe and not unpleasant. It is desirable that the diluent be white or colorless. Organic sugars such as, for example, mannitol, inositol, glucose or sucrose, comprise the preferred diluent. Mannitol is the most preferred diluent.

Other substances may be present in the improved snuff to enhance its pleasant qualities. For example, food coloring or artificial or natural flavors may be present to enhance the appearance, taste and scent of the nicotine mixture.

The improved snuff is prepared by the method comprising the steps of preparing a solution of nicotine, adding an acid to the solution which results in the formation of a water soluble nicotine salt, separating the nicotine salt from the solution, and diluting the nicotine salt to a usable concentration. The improved snuff is optionally colored or flavored by adding coloring and/or flavoring agents.

The nicotine used in preparing the improved snuff must be substantially pure. For the purposes of this disclosure, "substantially pure nicotine" is nicotine (d), nicotine (1), nicotine (d1), and/or nicotine salts which contain only minute, insignificant quantities of substances which are either water insoluble, carcinogenic, or contribute to the incidence of coronary heart disease. For example, ninety-eight percent nicotine (1) is commercially available from Eastman Chemical, stock number 1242.

The solvent used in preparing the improved snuff may be any solvent in which nicotine and the acid are soluble and from which the nicotine salt may be separated. This solvent may be aqueous or organic. If the nicotine salt is not completely dry, it is difficult to maintain the salt in a powder form. Preferably, the solvent will be one in which the nicotine and the acid are soluble and from which the nicotine salt can be crystalized. The most preferred solvent is ethyl alcohol, although in certain large commercial operations it is anticipated that water will be the preferred solvent.

The acid used in preparing the improved snuff may be any acid, organic or inorganic, which forms a salt with nicotine. Organic acids, such as oxalic, benzoic, or salicylic, are preferred to mineral acids because the mineral salts of nicotine are typically hygroscopic. The most preferred organic acid is oxalic acid.

The acid may be added to the nicotine solution neat or it may be first dissolved in a solvent. The solvent used for the acid solution may be the same solvent used for the nicotine solution or it may be a different solvent. When ethyl alcohol is the solvent in the nicotine solution, it is the preferred solvent for the acid solution. If ethyl alcohol is used, adding the acid solution to the nicotine solution will cause nicotine salts formed thereby to precipitate as a white crystal. Preferably the acid solution is saturated at room temperature to minimize the amount of solvent required.

The nicotine salt may be separated from the solution by any appropriate method, including, but not limited to, evaporation or filtration. The method that is preferred will be dependent on the type of material being manufactured, the size of the operation and the base materials. The nicotine salt may be filtered from the solution as it is formed. Preferably, filtration is facilitated by first heating the solution and then cooling it, forming larger crystals. The separation is completed by drying the nicotine salt. The crystals of nicotine salt are then crushed or ground into a powder form. In certain embodiment, in order to make a commercial product, the crystals may be washed prior to use, i.e. with ethyl ether or like material.

The diluent used in preparing the improved snuff may be added either before or after powdering the nicotine salt. The diluent should be water soluble, harmless and not unpleasant. Preferably, the diluent will be white or colorless. Organic sugars such as, for example, mannitol, glucose or sucrose, may be used. Mannitol is the most preferred diluent.

Other substances may be added to the improved snuff to enhance its pleasant qualities. For example, adding a coloring agent such as food coloring or a flavoring agent such as an artificial or natural tobacco flavoring may be present to enhance the appearance, taste and scent of the improved snuff.

EXAMPLE

Two milliliters of nicotine were added to 10 milliliters of absolute alcohol. In a separate container, anhydrous oxalic acid was added to 20 milliliters of ethyl alcohol until the solution was saturated at room temperature. Then, the oxalic acid solution was slowly added to the nicotine solution, forming a white precipitate, until no more precipitate formed. The resulting mixture was heated until the precipitate dissolved and was then allowed to cool slowly. White crystals formed in the container after cooling. The mother liquor was removed, and the resulting crystals were washed with anhydrous ethyl ether. These crystals, an oxalic salt of nicotine, were finely powdered and diluted to approximately a 3% concentration with powdered mannitol. The powdered mixture was flavored with 3 mg./g. tobacco flavor MT No. 1, manufactured by Comax Corporation and 1.125 mg./g. VA neutrals G3578994, manufactured by International Flavors and Fragrances, Inc.

While the novel improved snuff and preparation thereof is described above, many other variations may occur to those skilled in the art. Our invention includes all those variations which fall within the scope of the appended claims.

What is claimed is:

1. An improved snuff, useful in the nasal application of nicotine, comprising:
   (a) a substantially pure powdered nicotine salt; and
   (b) a powdered water soluble diluent.

2. The improved snuff of claim 1, further comprising a coloring agent in an effective amount.

3. The improved snuff of claim 1, further comprising a flavoring agent in an effective amount.

4. The improved snuff of claim 1, wherein said powdered nicotine salt consists essentially of:
   (i) nicotine; and
   (ii) an organic acid.

5. The improved snuff of claim 4, wherein said organic acid is oxalic acid.

6. The improved snuff of claim 1, wherein said diluent is a sugar.

7. The improved snuff of claim 1, wherein said nicotine salt is present in concentration of from 3% to 5% by weight of the improved snuff.

8. An improved snuff, useful in the nasal application of nicotine, comprising:
 (a) a substantially pure powdered nicotine oxalate salt wherein said salt is present in a concentration of from 3% to 5% by weight of said improved snuff; and
 (b) a powdered sugar.

9. The improved snuff of claim 8, further comprising a coloring agent in an effective amount.

10. The improved snuff of claim 8, further comprising a flavoring agent in an effective amount.

11. A method of preparing an improved snuff useful in the nasal application of nicotine, comprising the steps of:
 (a) providing a solvent in which nicotine is soluble and from which nicotine salts can be crystallized;
 (b) preparing a solution of substantially pure nicotine in said solvent;
 (c) adding an organic acid to said solution, whereby a water soluble nicotine salt is precipitated;
 (d) separating said precipitate from said solution;
 (e) drying said precipitate;
 (f) powdering said precipitate; and
 (g) combining said powdered precipitate with a solid, water soluble diluent in an amount sufficient to form an improved snuff having a nicotine salt concentration of from about 3% to about 5% by weight.

12. The method of preparing an improved snuff of claim 11, further comprising the step of coloring said improved snuff with a food coloring in an effective amount.

13. The method of preparing an improved snuff of claim 11, further comprising the step of flavoring said improved snuff with a flavoring agent in an effective amount.

14. The method of preparing an improved snuff of claim 11, wherein said solvent is an organic solvent.

15. The method of preparing an improved snuff of claim 11, wherein said solvent is ethyl alcohol.

16. The method of preparing an improved snuff of claim 11, wherein said acid is oxalic acid.

17. The method of preparing an improved snuff of claim 11, wherein said diluent is mannitol.

* * * * *